United States Patent
Fukumoto et al.

(10) Patent No.: US 11,555,005 B2
(45) Date of Patent: Jan. 17, 2023

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Naoya Fukumoto, Ichihara (JP); Ryuuta Miyasaka, Funabashi (JP); Hiroyuki Tomita, Ichihara (JP); Michio Seri, Ichihara (JP); Naoko Ito, Tokorozawa (JP); Katsumi Murofushi, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 560 days.

(21) Appl. No.: 16/489,896

(22) PCT Filed: Feb. 8, 2018

(86) PCT No.: PCT/JP2018/004411
§ 371 (c)(1),
(2) Date: Aug. 29, 2019

(87) PCT Pub. No.: WO2018/159250
PCT Pub. Date: Sep. 7, 2018

(65) Prior Publication Data
US 2020/0002258 A1    Jan. 2, 2020

(30) Foreign Application Priority Data
Mar. 2, 2017   (JP) .............................. JP2017-039820

(51) Int. Cl.
*C07C 43/13*     (2006.01)
*C08G 65/337*    (2006.01)
(Continued)

(52) U.S. Cl.
CPC .......... *C07C 43/137* (2013.01); *C08G 65/337* (2013.01); *G11B 5/7257* (2020.08); *C10M 107/38* (2013.01)

(58) Field of Classification Search
CPC ...... C07C 43/137; G11B 5/725; C08G 65/337
See application file for complete search history.

(56) References Cited

U.S. PATENT DOCUMENTS

| | | | |
|---|---|---|---|
| 2016/0068778 | A1 | 3/2016 | Conley et al. |
| 2022/0259513 | A1* | 8/2022 | Fukumoto .......... C08G 65/3318 |

FOREIGN PATENT DOCUMENTS

| | | |
|---|---|---|
| JP | 05-258287 A | 10/1993 |
| JP | 09-282642 A | 10/1997 |

(Continued)

OTHER PUBLICATIONS

X.-C. Guo et al., "A multidentate lubricant for use in hard disk drives at sub-nanometer thickness", Journal of Applied Physics, 2012, pp. 024503-1-024503-7, vol. 111.

(Continued)

*Primary Examiner* — Holly Rickman
(74) *Attorney, Agent, or Firm* — Sughrue Mion, PLLC

(57) ABSTRACT

A fluorine-containing ether compound according to the present invention is a fluorine-containing ether compound represented by the following General Formula (1).

[Chem. 1]

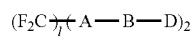

(1)

11 Claims, 1 Drawing Sheet

(51) Int. Cl.
    *G11B 5/725*    (2006.01)
    *C10M 107/38*   (2006.01)

(56) References Cited

FOREIGN PATENT DOCUMENTS

| JP | 2009-245491 A | 10/2009 |
| JP | 2012-007008 A | 1/2012 |
| WO | 2013/054393 A1 | 4/2013 |

OTHER PUBLICATIONS

International Search Repot for PCT/JP2018/004411, dated Apr. 17, 2018.

\* cited by examiner

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2018/004411 filed Feb. 8, 2018, claiming priority based on Japanese Patent Application No. 2017-039820 filed Mar. 2, 2017, the contents of which are incorporated herein by reference.

TECHNICAL FIELD

The present invention relates to a fluorine-containing ether compound, a lubricant for a magnetic recording medium, and a magnetic recording medium.

BACKGROUND ART

The development of magnetic recording media suitable for a high recording density has progressed in order to improve the recording density of magnetic recording and reproducing devices.

In the related art, magnetic recording media are known that have a recording layer or the like laminated on a substrate for a magnetic recording medium, a protective layer made of carbon or the like formed on the recording layer, and a lubricating layer additionally formed on the protective layer. The protective layer protects information recorded in the recording layer and improves the slidability of a magnetic head. However, it is not possible to obtain sufficient durability of a magnetic recording medium by simply providing a protective layer on the recording layer.

Therefore, generally, a lubricant is applied to the surface of the protective layer to form a lubricating layer. When the lubricating layer is provided on the protective layer, it is possible to prevent direct contact between the magnetic head of the magnetic recording and reproducing device and the protective layer and to significantly reduce a frictional force of the magnetic head that slides on the magnetic recording medium, thus improving durability.

Regarding a lubricant used for a magnetic recording medium such as a hard disk, for example, in Patent Document 1, a lubricant containing a fluorinated polyether having a polar group represented by $-(OCH_2CH_2)_nOH$ (here, n is an integer of 1 to 30) at at least one end of a fluorinated polyether including a $-C_mF_{2m}O$-unit (here, m is an integer of 1 to 18) as a basic framework has been proposed. In addition, similar chain compounds having a perfluoropolyether main chain and a polar group are disclosed in Patent Documents 2 to 4.

CITATION LIST

Patent Literature

[Patent Document 1]
Japanese Unexamined Patent Application, First Publication No. H5-258287
[Patent Document 2]
Japanese Unexamined Patent Application, First Publication No. H9-282642
[Patent Document 3]
Japanese Unexamined Patent Application, First Publication No. 2009-245491
[Patent Document 4]
Japanese Unexamined Patent Application, First Publication No. 2012-7008

SUMMARY OF INVENTION

Technical Problem

In order to improve a recording density of a magnetic recording and reproducing device and further reduce a flying height of a magnetic head of a magnetic recording and reproducing device, it is required to further reduce the thickness of a lubricating layer.

However, when the thickness of the lubricating layer is thin, gaps may be formed in the lubricating layer, the coverage of the surface of the magnetic recording medium by the lubricating layer may be reduced, and a part of a layer below the lubricating layer may be exposed.

When gaps are formed in the lubricating layer, environmental substances that generate contaminants may enter a layer below the lubricating layer from gaps in the lubricating layer, and the magnetic recording medium may become contaminated.

More specifically, when environmental substances that generate contaminants such as ionic impurities enter a layer below the lubricating layer from gaps in the lubricating layer, the environmental substances that have entered the layer below the lubricating layer cause ionic components present in the layer below the lubricating layer to aggregate and generate contaminants that contaminate the magnetic recording medium.

In addition, the inside of a hard disk drive including a magnetic recording medium generally reaches a high-temperature state when the magnetic recording medium is driven and information is recorded and reproduced in the magnetic recording medium. Entering of environmental substances from gaps in the lubricating layer, aggregation of ionic components present in a layer below the lubricating layer, and generation of contaminants that contaminate the magnetic recording medium described above are more significant under high-temperature conditions. In addition, there is no recognition of such problems in the above Patent Documents 1 to 4.

The present invention has been made in view of the above circumstances, and an objective of the present invention is to provide a fluorine-containing ether compound in which, even if the thickness is thin, it is possible to form a lubricating layer that can cover the surface of a protective layer with high coverage, it is possible to prevent aggregation of ionic components present in a layer below the lubricating layer caused by environmental substances that have entered the layer below the lubricating layer, it is possible to reduce the generation of contaminants that contaminate the magnetic recording medium, and it is possible to effectively prevent contamination on the surface of the magnetic recording medium and prevent adhesion (transfer) of contaminants present on the magnetic recording medium to the magnetic head, a lubricant for a magnetic recording medium including the fluorine-containing ether compound, and a magnetic recording medium using the lubricant for a magnetic recording medium.

Solution to Problem

In order to solve the above problems, the inventors conducted extensive studies.

As a result, it was found that it is sufficient that a compound having a chain structure composed of a difluoromethylene group ($-CF_2-$) at the center, having a perfluoropolyether chain at both ends of the chain structure via a linking group including at least one polar group, and having a structure in which a unit having a hydroxyl group is bonded to the end of the perfluoropolyether chain is applied as a lubricant. In addition, it was found that, when a lubricating layer is formed on the protective layer of the magnetic recording medium using the lubricant, the lubricating layer and the protective layer are bonded with a strong bonding strength, the thickness of the lubricating layer can be made sufficiently thin, and the surface of the protective layer can be covered with the lubricating layer with a substantially uniform film thickness and with high coverage, and thereby the present invention shown in the following [1] to [13] was completed.

[1] A fluorine-containing ether compound according to an embodiment of the present invention is represented by the following General Formula (1):

[Chem. 1]

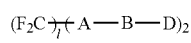

(1)

(In the formula, A is a linking group including at least one polar group, B is any of the following Formula (2), the following Formula (3), the following Formula (4) and the following Formula (5), D is any of a hydroxyl group, the following Formula (6), the following Formula (7) and the following Formula (8), and l is an integer of 1 to 10.)

[Chem. 2]

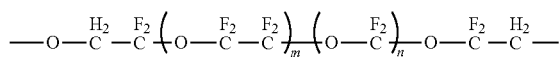

(2)

(In the formula, m is an integer of 1 to 30, and n is an integer of 1 to 30. In Formula (2), an arrangement sequence of two repeating units ($O-CF_2$) and ($O-CF_2-CF_2$) is not particularly limited, and the sequence shown in Formula (2) may be reversed.)

[Chem. 3]

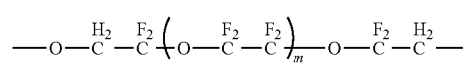

(3)

(In the formula, p is an integer of 1 to 30.)

[Chem. 4]

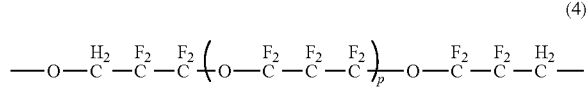

(4)

(In the formula, p is an integer of 1 to 30.)

[Chem. 5]

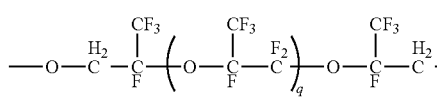

(5)

(In the formula, q is an integer of 1 to 30.)

[Chem. 6]

(6)

(In the formula, r is an integer of 0 to 5.)

[Chem. 7]

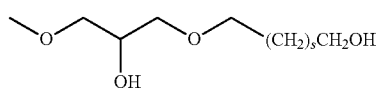

(7)

(In the formula, s is an integer of 0 to 5.)

[Chem. 8]

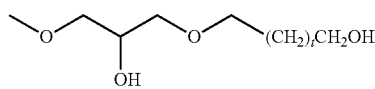

(8)

(In the formula, t is an integer of 1 to 5.)

[2] In the fluorine-containing ether compound according to [1], preferably, A in General Formula (1) is a linking group having at least one polar group and having 1 to 20 carbon atoms.

[3] In the fluorine-containing ether compound according to [2], preferably, A in General Formula (1) is a linking group represented by the following Formula (9):

[Chem. 9]

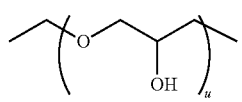

(9)

(In the formula, u is an integer of 1 to 5.)

[4] In the fluorine-containing ether compound according to any one of [1] to [3], preferably, the number-average molecular weight is in a range of 1,000 to 10,000.

[5] In the fluorine-containing ether compound according to any one of [1] to [4], preferably, the compound represented by General Formula (1) is represented by the following Formula (10):

[Chem. 10]

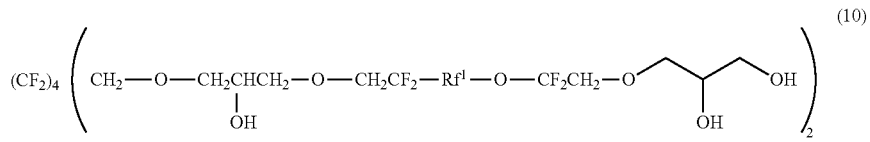

(In the formula, $Rf^1$ is represented by the following Formula (11), and each of m and n is an integer of 1 to 30.)

[Chem. 11]

[6] In the fluorine-containing ether compound according to any one of [1] to [4], preferably, the compound represented by General Formula (1) is represented by the following Formula (12):

[Chem. 12]

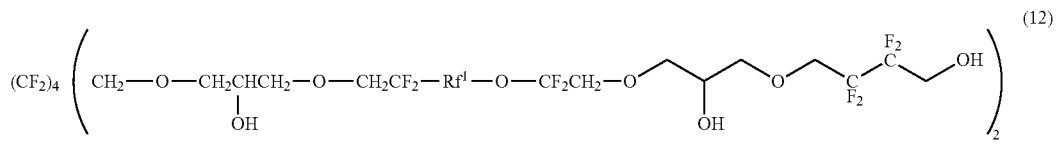

(In the formula, $Rf^1$ is represented by the following Formula (11), and each of m and n is an integer of 1 to 30.)

[Chem. 13]

[7] In the fluorine-containing ether compound according to any one of [1] to [4], preferably, the compound represented by General Formula (1) is represented by the following Formula (13):

[Chem. 14]

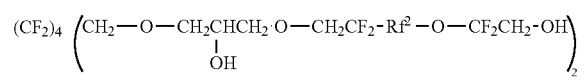

(In the formula, $Rf^2$ is represented by the following Formula (14), and m is an integer of 1 to 30.)

[Chem. 15]

[8] In the fluorine-containing ether compound according to any one of [1] to [4], preferably, the compound represented by General Formula (1) is represented by the following Formula (15):

[Chem. 16]

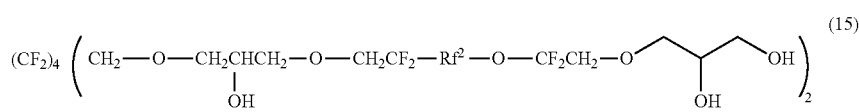

(In the formula, $Rf^2$ is represented by the following Formula (14), and m is an integer of 1 to 30.)

[Chem. 17]

$$-(OCF_2CF_2)_m- \quad (14)$$

[9] In the fluorine-containing ether compound according to any one of [1] to [4], preferably, the compound represented by General Formula (1) is represented by the following Formula (16):

[Chem. 18]

(16)

(In the formula, $Rf^2$ is represented by the following Formula (14), and m is an integer of 1 to 30.)

[Chem. 19]

$$-(OCF_2CF_2)_m- \quad (14)$$

[10] In the fluorine-containing ether compound according to any one of [1] to [4], preferably, the compound represented by General Formula (I) is represented by the following Formula (17):

[Chem. 20]

(17)

(In the formula, $Rf^1$ is represented by the following Formula (11), and each of m and n is an integer of 1 to 30.)

[Chem. 21]

$$-(OCF_2CF_2)_m(OCF_2)_n- \quad (11)$$

[11] A lubricant for a magnetic recording medium according to an embodiment of the present invention includes the fluorine-containing ether compound according to any one of [1] to [10].
[12] A magnetic recording medium according to an embodiment of the present invention is a magnetic recording medium in which at least a magnetic layer, a protective layer, and a lubricating layer are sequentially provided on a substrate, and the lubricating layer consists of the lubricant for a magnetic recording medium according to [11].
[13] In the magnetic recording medium according to [12], preferably, the average film thickness of the lubricating layer is 0.5 nm to 3 nm.

Advantageous Effects of Invention

When the fluorine-containing ether compound of the present invention is applied as a lubricant for a magnetic recording medium, even if the thickness is thin, it is possible to form a lubricating layer that can cover the surface of the protective layer with high coverage. Therefore, in the magnetic recording medium using the lubricant for a magnetic recording medium of the present invention, it is possible to prevent aggregation of ionic components present in a layer below the lubricating layer caused by environmental substances that have entered the layer below the lubricating layer and it is possible to reduce the generation of contaminants that contaminate the magnetic recording medium. As a result, it is possible to effectively prevent contamination on the surface of the magnetic recording medium and prevent adhesion (transfer) of contaminants present on the magnetic recording medium to the magnetic head.

DESCRIPTION OF EMBODIMENTS

Figure 1:
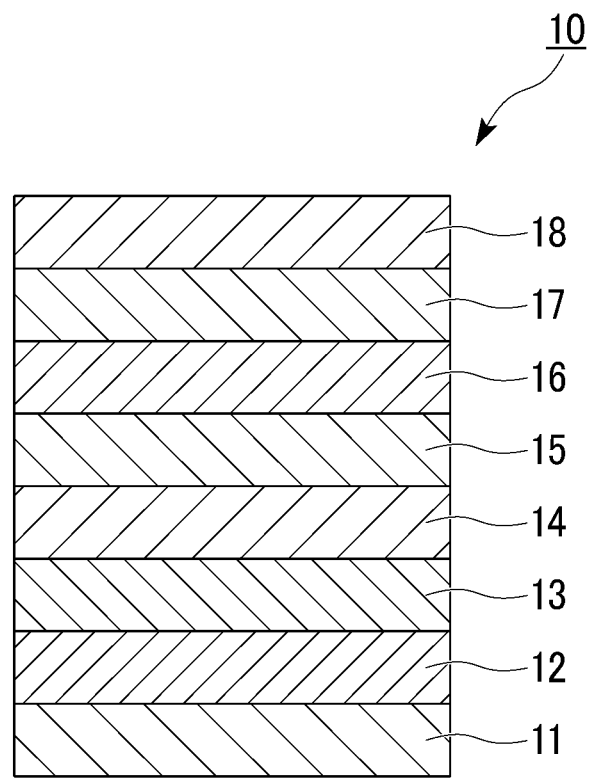
FIG. 1 is a schematic cross-sectional view showing an embodiment of a magnetic recording medium of the present invention.

Preferable embodiments of the present invention will be described below with reference to the drawings. However, the present invention is not limited to these embodiments. Unless otherwise specified, numbers, positions, materials and the like may be selected as necessary.
[Fluorine-Containing Ether Compound]
A fluorine-containing ether compound (an ether compound containing fluorine) of the present embodiment is a compound represented by the following General Formula (1).
This compound has a chain structure composed of a difluoromethylene group ($-CF_2-$) at the center, and has a perfluoropolyether chain B at both ends of the chain structure via a divalent or higher-valent linking group A including at least one polar group, and has a structure in which a unit D having a hydroxyl group at the end is bonded. That is, in this compound, A. B, and D are sequentially bonded to ends of the chain structure of the difluoromethylene group at the center.

[Chem. 22]

$$(F_2C)_l(A-B-D)_2 \quad (1)$$

(In the formula, A is a linking group including at least one polar group, B is any of the following Formula (2), the following Formula (3), the following Formula (4) and the following Formula (5), D is any of a hydroxyl group, the following Formula (6), the following Formula (7) and the following Formula (8), and l is an integer of 1 to 10.)

[Chem. 23]

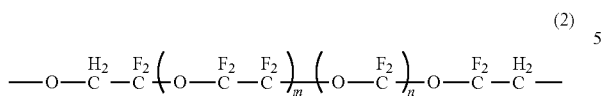
(2)

(In the formula, m is an integer of 1 to 30, and n is an integer of 1 to 30. In Formula (2), an arrangement sequence of the two repeating units is not particularly limited, and the sequence shown in Formula (2) may be reversed.)

[Chem. 24]

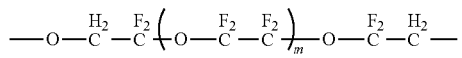
(3)

(In the formula, m is an integer of 1 to 30.)

[Chem. 25]

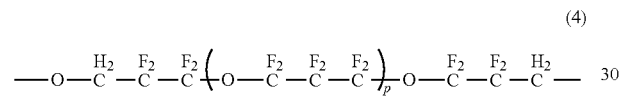
(4)

(In the formula, p is an integer of 1 to 30.)

[Chem. 26]

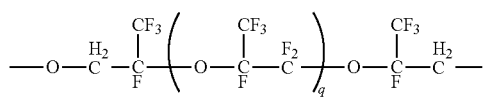
(5)

(In the formula, q is an integer of 1 to 30.)

[Chem. 27]

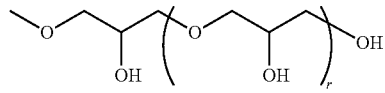
(6)

(In the formula, r is an integer of 0 to 5.)

[Chem. 28]

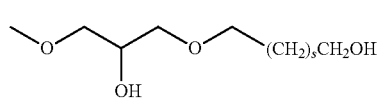
(7)

(In the formula, s is an integer of 0 to 5.)

[Chem. 29]

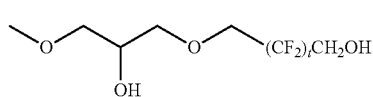
(8)

(In the formula, t is an integer of 1 to 5.)

In General Formula (1), l is preferably 3 to 8 and more preferably 4 to 6.

In General Formula (1), l is appropriately adjusted according to the performance required for a lubricant of the present embodiment such as silicone contamination resistance.

In General Formula (1). A may be a linking group, having 1 to 20 carbon atoms and at least one polar group, which bonds the above chain structure composed of the difluoromethylene group ($-CF_2-$) to the fluorine-containing ether group to be described below. Examples of the polar group include a hydroxyl group, a carboxyl group, an amino group, and an aminocarbonyl group. A is preferably a linking group represented by the following Formula (9).

[Chem. 30]

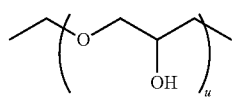
(9)

(In the formula, u is an integer of 1 to 5.)

In General Formula (1), when A is represented by Formula (9), u is 1 to 5, and preferably 1 to 3, and more preferably 1 or 2.

The structure of A in General Formula (1) and u in Formula (9) are appropriately adjusted according to the performance required for a lubricant of the present embodiment such as silicone contamination resistance.

In General Formula (1), when B is represented by Formula (2), m is preferably 3 to 20 and more preferably 4 to 10. In addition, n is preferably 3 to 20 and more preferably 4 to 10.

In Formula (2), an arrangement sequence of the two repeating units is not particularly limited, and the sequence shown in Formula (2) may be reversed.

In General Formula (1), when B is represented by Formula (3), m is preferably 3 to 20 and more preferably 4 to 10.

In General Formula (1), when B is represented by Formula (4), p is preferably 3 to 20 and more preferably 4 to 10.

In General Formula (1), when B is represented by Formula (5), q is preferably 3 to 20 and more preferably 4 to 10.

m, n, p and q of B in General Formulae (2) to (5) are appropriately adjusted according to the performance required for a lubricant of the present embodiment such as silicone contamination resistance.

In General Formula (1). D is represented by a hydroxyl group or any of Formulae (6) to (8).

In General Formula (1), when D is represented by Formula (6), r is preferably 0 to 4 and more preferably 0 to 2.

In General Formula (1), when D is represented by Formula (7), s is preferably 1 to 4 and more preferably 1 to 2.

In General Formula (1), when D is represented by Formula (8), t is preferably 1 to 4 and more preferably 1 to 2.

The structure of D in General Formula (1), r in Formula (6), s in Formula (7), and t in Formula (8) are appropriately adjusted according to the performance required for a lubricant of the present embodiment such as silicone contamination resistance.

The number-average molecular weight of the compound represented by General Formula (1) is preferably in a range of 1,000 to 10,000. The number-average molecular weight is more preferably in a range of 2,000 to 6,000 and most preferably in a range of 2,000 to 4,000.

When the number-average molecular weight of the compound represented by General Formula (1) exceeds 10,000, the viscosity may be high and it may be difficult to handle it. On the other hand, when the number-average molecular weight of the compound represented by General Formula (1) is less than 1,000, the lubricant easily evaporates from the substrate, the evaporated lubricant adheres to a magnetic head, and a load may be applied to a hard disk drive.

The number-average molecular weight can be obtained by gel permeation chromatography (GPC).

The measurement conditions of GPC are as follows.

Column: KF803 commercially available from Shodex, eluent: fluorinated solvent (product name: Asahiklin AK-225, commercially available from AGC Inc.)/acetone=4/1 (v/v), flow rate: 1 mL/min, detector: ELSD.

In addition, in the lubricant of the present embodiment, other known compounds used as a lubricant may be contained as long as the characteristics of including the compound represented by General Formula (1) are not impaired.

Examples of such a compound include a fluorine-containing ether compound other than the compound represented by General Formula (1) and a fluorine-containing ether compound having other functional groups. A lubricant containing a fluorine-containing ether compound other than the compound represented by General Formula (1) is referred to as "other lubricant." In the lubricant of the present embodiment, these other lubricants can be used by being mixed in as necessary. Specific examples of other lubricants include FOMBLIN (registered trademark) ZDIAC, FOMBLIN ZDEAL, FOMBLIN AM-2001 (all are commercially available from Solvey Solexis), and Moresco A20H (commercially available from Moresco). Regarding other lubricants, those having a number-average molecular weight of 1,000 to 10,000 are preferably used.

When the other lubricant is used in combination, the content of the fluorine-containing ether compound represented by General Formula (1) in the lubricant of the present embodiment is preferably 50 mass % or more and more preferably 70 mass % or more.

When a lubricating layer of the present embodiment including the compound of General Formula (1) is formed on a protective layer made of carbon or silicon carbide, at least one polar group present in each of two linking groups A constituting the compound and two hydroxyl groups are strongly bonded to carbon atoms contained in the protective layer. As a result, the lubricating layer and the protective layer can be bonded with a strong bonding strength. Therefore, the thickness of the lubricating layer can be made sufficiently thin.

That is, according to the lubricant of the present embodiment, even if the thickness is thin, the lubricating layer formed by application does not form an island shape or a mesh shape, and it is possible to form a lubricating layer in which the surface of the protective layer is covered with high coverage with a substantially uniform thickness. In addition, the formed lubricating layer has a function of preventing environmental substances, which generate contaminants such as ionic impurities, from entering from gaps into layers constituting a magnetic recording medium. Therefore, according to the lubricating layer of the present embodiment, it is possible to provide a magnetic recording medium with few contaminants present on the surface.

[Magnetic Recording Medium]

FIG. 1 is a schematic cross-sectional view showing an embodiment of a magnetic recording medium of the present invention.

A magnetic recording medium 10 of the present embodiment has a structure in which an adhesion layer 12, a soft magnetic layer 13, a first underlayer 14, a second underlayer 15, a magnetic layer 16, a protective layer 17 and a lubricating layer 18 are sequentially provided on a substrate 11.

"Substrate"

Regarding the substrate 11, a nonmagnetic substrate in which a film made of NiP or a NiP alloy is formed on a base made of a metal or an alloy material such as Al or an Al alloy can be used.

In addition, regarding the substrate 11, a nonmagnetic substrate made of a non-metallic material such as glass, a ceramic, silicon, silicon carbide, carbon, or a resin may be used, and a nonmagnetic substrate in which a film made of NiP or a NiP alloy is formed on a base made of such a non-metallic material may be used.

"Adhesion Layer"

The adhesion layer 12 is a layer for preventing the corrosion of the substrate 11 from progressing, when it is disposed in contact with the substrate 11 and the soft magnetic layer 13 provided on the adhesion layer 12.

The material of the adhesion layer 12 can be appropriately selected from, for example, Cr, Cr alloys, Ti, and Ti alloys.

The adhesion layer 12 can be formed by, for example, a sputtering method.

"Soft Magnetic Layer"

The soft magnetic layer 13 preferably has a structure in which a first soft magnetic film, an intermediate layer made of a Ru film, and a second soft magnetic film are sequentially laminated. That is, the soft magnetic layer 13 preferably has a structure in which an intermediate layer made of a Ru film is interposed between two soft magnetic film layers, and the soft magnetic films above and below the intermediate layer are bonded via anti-ferro-coupling (AFC). When the soft magnetic layer 13 has an AFC-bonded structure, it is possible to increase the resistance with respect to an external magnetic field, and the resistance with respect to a wide area tack erasure (WATE) phenomenon, which is a problem unique to perpendicular magnetic recording.

The first soft magnetic film and the second soft magnetic film are preferably a film made of a CoFe alloy.

When the first soft magnetic film and the second soft magnetic film are a film made of a CoFe alloy, a high saturation magnetic flux density Bs (1.4 (T) or more) can be realized.

In addition, any of Zr, Ta, and Nb is preferably added to a CoFe alloy used for the first soft magnetic film and the second soft magnetic film. Therefore, the amorphization of the first soft magnetic film and the second soft magnetic film can be promoted, the orientation of the seed layer can be improved, and the flying height of the magnetic head can be reduced.

The soft magnetic layer 13 can be formed by, for example, a sputtering method.

"First Underlayer"

The first underlayer 14 is a layer for controlling the orientation and crystal size of the second underlayer 15 and the magnetic layer 16 provided thereon, and is provided to increase the direction component perpendicular to the surface of the substrate of a magnetic flux generated from the magnetic head and to fix the direction of magnetization of the magnetic layer 16 more firmly to a direction perpendicular to the substrate 11.

The first underlayer 14 is preferably a layer made of a NiW alloy. When the first underlayer 14 is a layer made of a NiW alloy, other elements such as B, Mn, Ru, Pt, Mo, and Ta may be added to the NiW alloy as necessary.

The first underlayer 14 can be formed by, for example, a sputtering method.

"Second Underlayer"

The second underlayer 15 is a layer that performs control such that the orientation of the magnetic layer 16 becomes favorable. The second underlayer 15 is preferably a layer made of Ru or a Ru alloy.

The second underlayer 15 may be composed of a single layer or a plurality of layers. When the second underlayer 15 is composed of a plurality of layers, all the layers may be made of the same material or at least one layer may be made of different materials.

The second underlayer 15 can be formed by, for example, a sputtering method.

"Magnetic Layer"

The magnetic layer 16 is preferably made of a magnetic film in which the axis of easy magnetization is in a direction perpendicular to the surface of the substrate. The magnetic layer 16 is a layer containing Co and Pt and also may be a layer containing an oxide, Cr, B, Cu, Ta, Zr, or the like in order to further improve SNR characteristics.

Examples of the oxide contained in the magnetic layer 16 include $SiO_2$, SiO, $Cr_2O_3$, CoO, $Ta_2O_3$, and $TiO_2$.

The magnetic layer 16 may be composed of one layer and may be composed of a plurality of layers made of materials with different compositions.

For example, when the magnetic layer 16 is composed of three layers including a first magnetic layer, a second magnetic layer, and a third magnetic layer, the first magnetic layer preferably has a granular structure made of a material containing Co, Cr, and Pt and additionally containing an oxide. Regarding the oxide contained in the first magnetic layer, for example, oxides of Cr, Si, Ta. Al, Ti, Mg, Co, and the like, are preferably used. Among these, in particular, $TiO_2$, $Cr_2O_3$, $SiO_2$, and the like can be suitably used. In addition, the first magnetic layer is preferably made of a composite oxide in which two or more types of oxide are added. Among these, in particular, $Cr_2O_3$—$SiO_2$. $Cr_2O_3$—$TiO_2$, $SiO_2$—$TiO_2$ and the like can be suitably used.

The first magnetic layer can contain one or more elements selected from among B, Ta, Mo, Cu, Nd, W, Nb, Sm, Tb, Ru, and Re in addition to Co, Cr, Pt, and an oxide.

When the above elements are contained, it is possible to promote refinement of magnetic particles or improve the crystallinity and orientation, and obtain recording and reproducing characteristics and thermal fluctuation characteristics suitable for higher density recording.

The same materials as for the first magnetic layer can be used for the second magnetic layer. The second magnetic layer preferably has a granular structure.

In addition, the third magnetic layer preferably has a non-granular structure made of a material containing Co, Cr, and Pt and containing no oxide. The third magnetic layer contains one or more elements selected from among B, Ta. Mo. Cu, Nd. W, Nb, Sm, Tb, Ru. Re, and Mn in addition to Co, Cr, and Pt. When the third magnetic layer contains the above elements in addition to Co, Cr, and Pt, it is possible to promote refinement of magnetic particles or improve the crystallinity and orientation, and obtain recording and reproducing characteristics and thermal fluctuation characteristics suitable for higher density recording.

In addition, when the magnetic layer 16 is composed of a plurality of layers, a non-magnetic layer is preferably provided between adjacent magnetic layers. When the magnetic layer 16 is composed of three layers including a first magnetic layer, a second magnetic layer, and a third magnetic layer, a non-magnetic layer is preferably provided between the first magnetic layer and the second magnetic layer, and between the second magnetic layer and the third magnetic layer.

When a non-magnetic layer with an appropriate thickness is provided between magnetic layers, it is possible to easily invert the magnetization of each film, it is possible to reduce the dispersion of magnetization inversion of all magnetic particles, and it is possible to further improve an S/N ratio.

For example, Ru, a Ru alloy, a CoCr alloy, a CoCrX1 alloy (X1 is at least one, two or more elements selected from among Pt, Ta, Zr, Re, Ru, Cu, Nb, Ni, Mn, Ge, Si, O, N, W, Mo, Ti, V, Zr, and B), or the like can be suitably used for the non-magnetic layer provided between the magnetic layers 16.

In addition, an alloy material containing an oxide, a metal nitride, or a metal carbide is preferably used for the non-magnetic layer provided between the magnetic layers 16. Specifically, regarding the oxide, for example, $SiO_2$, $Al_2O_3$, $Ta_2O_5$, $Cr_2O_3$, MgO, $Y_2O_3$, $TiO_2$ or the like can be used. Regarding the metal nitride, for example, AlN, $Si_3N_4$, TaN, CrN or the like can be used. Regarding the metal carbide, for example, TaC, BC, SiC or the like can be used.

The non-magnetic layer can be formed by, for example, a sputtering method.

In addition, in order to realize a higher recording density, the magnetic layer 16 is preferably a magnetic layer for perpendicular magnetic recording in which the axis of easy magnetization is in a direction perpendicular to the surface of the substrate, but may be for in-plane magnetic recording.

The magnetic layer 16 may be formed by any conventionally known method such as a vapor deposition method, an ion beam sputtering method, and a magnetron sputtering method, but it is generally formed by a sputtering method.

"Protective Layer"

The protective layer 17 is a layer for protecting the magnetic layer 16. The protective layer 17 may be composed of one layer or may be composed of a plurality of layers. The protective layer 17 is a carbon-based protective layer (a layer made of carbon or silicon carbide) and is preferably made of carbon.

The lubricating layer 18 formed on the protective layer 17 is a layer having a very strong bonding strength with carbon.

When the protective layer 17 is made of carbon or a silicon carbide, carbon atoms contained in the protective layer 17 and the lubricating layer 18 are bonded, and the protective layer 17 and the lubricating layer 18 are bonded with a strong bonding strength. As a result, even if the thickness of the lubricating layer 18 is thin, a magnetic recording medium 10 in which the surface of the protective layer 17 is covered with high coverage is obtained, and it is possible to effectively prevent contamination on the surface of the magnetic recording medium 10.

In particular, when the protective layer 17 is made of carbon, a bonding strength between the lubricating layer 18 and the protective layer 17 due to bonding between carbon atoms contained in the protective layer 17 and the lubricating layer 18 is further improved. Therefore, when the protective layer 17 is made of carbon, it is possible to more effectively prevent contamination on the surface of the magnetic recording medium 10, and even if the thickness of the lubricating layer 18 is thinner, the surface of the protective layer 17 can be sufficiently covered with high coverage.

Regarding a film formation method of the protective layer 17, a sputtering method using a carbon target material, a chemical vapor deposition (CVD) method using a hydrocarbon material such as ethylene and toluene, an ion beam deposition (IBD) method, or the like can be used.

"Lubricating Layer"

The lubricating layer 18 is a layer that prevents contamination of the magnetic recording medium 10, reduces a frictional force of the magnetic head of the magnetic recording and reproducing device that slides on the magnetic recording medium 10, and improves the durability of the magnetic recording medium 10.

As shown in FIG. 1, the lubricating layer 18 is a layer that is in contact with and formed on the protective layer 17 and consists of a lubricant for a magnetic recording medium of the above embodiment.

The average film thickness of the lubricating layer 18 is preferably 0.5 nm (5 Å) to 3 nm (30 Å) and more preferably 0.5 nm (5 Å) to 2 nm (20 Å).

When the average film thickness of the lubricating layer 18 is set to 0.5 nm or more, the surface of the protective layer 17 can be covered with high coverage with a uniform film thickness without making the lubricating layer 18 into an island shape or a mesh shape.

In addition, when the average film thickness of the lubricating layer 18 is 3 nm or less, the flying height of the magnetic head can be sufficiently reduced and the recording density of the magnetic recording medium 10 can be increased.

When the surface of the protective layer 17 is not sufficiently covered with the lubricating layer 18 with high coverage, water containing environmental substances that generate contaminants such as ionic impurities adsorbed to the surface of the magnetic recording medium 10 passes through gaps in the lubricating layer 18 and enters below the lubricating layer 18. The environmental substances that have entered the layer below the lubricating layer 18 cause fine ionic components hidden under the lubricating layer 18 to aggregate to generate ionic contaminants. Then, during magnetic recording and reproducing, the contaminants (aggregated components) adhere (transfer) to the magnetic head, the magnetic head is damaged, and magnetic recording and reproducing characteristics of the magnetic recording and reproducing device deteriorate.

Such a problem caused when environmental substances enter from gaps in the lubricating layer 18 appears more significantly when the magnetic recording medium 10 is stored under high-temperature conditions.

The environmental substances that generate contaminants are, for example, ionic impurities. Examples of metal ions contained in ionic impurities include sodium ions and potassium ions. Examples of inorganic ions contained in ionic impurities include chloride ions, bromine ions, nitrate ions, sulfate ions, ammonium ions, oxalate ions, and formate ions.

"Method of Forming a Lubricating Layer"

The lubricating layer 18 is formed, for example, by preparing a magnetic recording medium during production in which respective layers up to the protective layer 17 are formed on the substrate 11, and applying a solution for forming a lubricating layer to the protective layer 17 in the magnetic recording medium during production.

The solution for forming a lubricating layer is obtained by diluting the lubricant for a magnetic recording medium of the above embodiment in a solvent to obtain a viscosity and a concentration suitable for the coating method.

Examples of the solvent used for the solution for forming a lubricating layer include a fluorine solvent such as Vertrel (registered trademark) XF (product name, commercially available from Du Pont-Mitsui Fluorochemicals Co., Ltd.).

A method of applying a solution for forming a lubricating layer is not particularly limited, and examples thereof include a spin coating method and a dip method.

When a dip method is used, for example, the following processes are performed. The substrate 11 in which respective layers up to the protective layer 17 are formed is immersed in a solution for forming a lubricating layer that is put into an immersion tank of a dip coating device, and the substrate 11 is then pulled up from the immersion tank at a predetermined speed. In this way, the solution for forming a lubricating layer can be applied to the surface on the protective layer 17 of the substrate 11. When a dip method is used, the solution for forming a lubricating layer can be uniformly applied to the surface on the protective layer 17 of the substrate 11 and the lubricating layer 18 with a uniform film thickness can be formed on the protective layer 17.

In the magnetic recording medium 10 of the present embodiment, at least the magnetic layer 16, the protective layer 17, and the lubricating layer 18 are sequentially provided, the protective layer 17 is made of carbon or a silicon carbide, the lubricating layer 18 is in contact with and formed on the protective layer 17, and the lubricating layer 18 contains a lubricant for a magnetic recording medium of the above embodiment. The lubricant includes at least one polar group present in each of two linking groups A of the fluorine-containing ether compound represented by General Formula (1) and at least one hydroxyl group present in each of two ends D. When at least one polar group present in each of two linking groups A and at least one hydroxyl group present in each of two ends D are strongly bonded to carbon atoms contained in the protective layer 17, since the lubricating layer 18 and the protective layer 17 are bonded with a strong bonding strength, the thickness of the lubricating layer 18 can be made sufficiently thin.

That is, the magnetic recording medium 10 of the present embodiment has the lubricating layer 18 in which the surface of the protective layer 17 can be covered with high coverage with a substantially uniform film thickness without forming an island shape or a mesh shape even if the lubricant coating thickness is thin, and prevents environmental substances that generate contaminants such as ionic impurities from entering from gaps in the lubricating layer 18. Therefore, in the magnetic recording medium 10 of the present embodiment, the amount of contaminants present on the surface is reduced.

EXAMPLES

While the present invention will be described below in further detail with reference to examples and a comparative example, the present invention is not limited to the following examples.

Example 1

(Synthesis of Compound)

1 g of 2,2,3,3,4,4,5,5-octafluorohexane-1,6-diol, 19 mL of acetone, and 19.8 g of a sodium hydroxide aqueous solution (NaOH/water=0.8 g/19 g) were put into a 100 mL eggplant flask, and the mixture was heated at 70° C. and stirred for 1 hour while refluxing.

Next, 15 mL of epichlorohydrin was added to the mixture, and additionally heated at 70° C. and stirred for 5 hours while refluxing.

Then, the mixture was cooled to 25° C. and neutralized with hydrochloric acid, and a fluorinated solvent (product name: Asahiklin (registered trademark) AK-225, commercially available from AGC Inc.) was then added thereto, and the mixture was washed with water.

Next, an organic phase in the eggplant flask was collected and magnesium sulfate was added to the organic phase for dehydration and filtration was performed by a filter.

Next, the solvent was distilled off from the filtrate using an evaporator, and column purification was additionally performed, and thereby a colorless and transparent liquid compound 1 (1.2 g) including a compound represented by the following Formula (18) was obtained.

$^1$H-NMR measurement and $^{19}$F-NMR measurement of the obtained compound 1 were performed, and the structure was identified based on the following results.

$^1$H-NMR (400 MHz, hexafluorobenzene/acetone-D$_6$=4/1 (v/v)): δ(ppm)=2.60 (2H), 2.77 (2H), 3.10 to 3.15 (2H), 3.54 (2H), 3.92 to 4.20 (6H)

$^{19}$F-NMR (400 MHz, hexafluorobenzene/acetone-D6=4/1 (v/v)): δ(ppm)=−125.43 (4F), −122.15 (4F)

[Chem. 31]

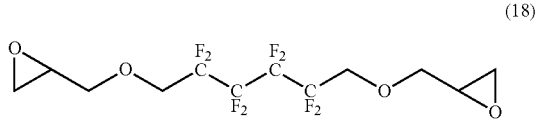

(18)

Under a nitrogen atmosphere, the compound 1 (1 g) and 22 g of a fluoropolyether represented by HO—CH$_2$CF$_2$(OCF$_2$CF$_2$)$_m$(OCF$_2$)$_n$OCF$_2$CH$_2$OH (m=1 to 7, n=1 to 7, a number-average molecular weight of 800 and a molecular weight distribution of 1.1) were put into a 100 mL eggplant flask, and the mixture was stirred until it became uniform.

Next, 1.8 g of potassium tert-butoxide was added to the mixture and stirred for 8 hours while heating at 70° C.

Then, the mixture was cooled to 25° C. and neutralized with hydrochloric acid, and a fluorinated solvent (product name: Asahiklin (registered trademark) AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator, and supercritical extraction was then performed under conditions of 60° C. and 18 MPa. and thereby a colorless and transparent liquid compound 2a (4.5 g) including a compound represented by the following Formula (17) was obtained. Here, Rf$^1$ in the following Formula (17) is represented by the following Formula (11).

$^1$H-NMR measurement and $^{19}$F-NMR measurement of the obtained compound 2a were performed, and the structure was identified based on the following results.

$^1$H-NMR (400 MHz, hexafluorobenzene/acetone-D6=4/1 (v/v)): δ(ppm)=3.72 to 3.88 (8H), 3.88 to 4.04 (6H), 4.05 to 4.22 (8H)

$^{19}$F-NMR (400 MHz, hexafluorobenzene/acetone-D6=4/1 (v/v)): δ(ppm)=−124.09 (4F), −120.70 (4F), −91.00 to −88.49 (27F), −83.19 (2F), −81.13 (2F), −80.61 (2F), −78.58 (2F), −55.65 to −51.37 (12F)

[Chem. 32]

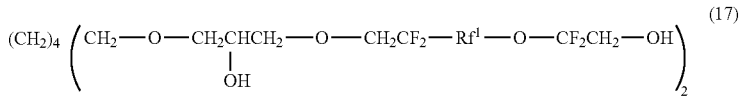

(17)

[Chem. 33]

(11)

(Evaluation of Silicone Contamination Resistance)

The compound 2a was dissolved in Vertrel (registered trademark) XF (product name, commercially available from Du Pont-Mitsui Fluorochemicals Co., Ltd.), a diluted solution of the compound 2a was prepared so that the film thickness during coating was 10 Å to 15 Å, and applied to the protective layer of the magnetic recording medium with a diameter of 65 mm having a configuration shown in FIG. 1 according to a dip method.

In this case, the diluted solution was applied to the protective layer under conditions of an immersion speed of 10 mm/sec, an immersion time of 30 sec, and a pulling speed of 1.2 mm/sec according to a dip method, and thereby a lubricating layer including the compound 2a was formed.

The film thickness of the lubricating layer was measured using FT-IR (product name: Nicolet iS50, commercially available from Thermo Fisher Scientific).

Next, a load/unload (LUL) type hard disk drive was prepared and a magnetic recording medium in which a lubricating layer was formed was mounted. Regarding the head, a perpendicular magnetic recording head was used.

A commercially available silicone rubber gel tip (1 cm×1 cm×0.5 cm) was put into the hard disk drive, and a continuous LUL operation was repeated under the following environment.

Figure 2:
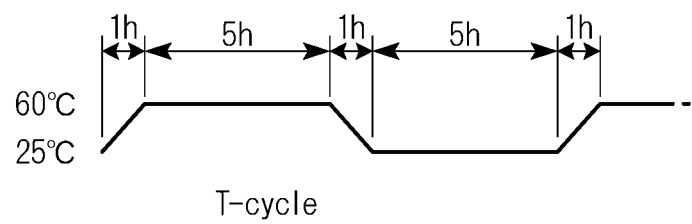
FIG. 2 is a diagram showing an environment in which a continuous load/unload (LUL) operation is repeated in examples and a comparative example.

A cycle operation (1 hour each for startup and shutdown) for 5 hours under a dry (relative humidity of 10% or less) environment of 25° C.→60° C.→25° C. was continued until the following problems occurred (refer to FIG. 2).

A time at which a drive current of a spindle motor of the hard disk drive exceeded a threshold value was determined as an endurance time. When the lubricating layer including the compound 2a was uniform without gaps, a cyclic siloxane vaporized from the silicone rubber gel tip was prevented from adhering to the magnetic recording medium, no load was applied to the spindle motor of the hard disk drive, and as a result, the endurance time became longer. On the other hand, when there were gaps in the lubricating layer including the compound 2a, the vaporized cyclic siloxane adhered to the magnetic recording medium, a load was applied to the spindle motor of the hard disk drive, and the endurance time became shorter.

When the endurance time was 150 hours or longer, this was evaluated as "○" when the endurance time was 100 hours or longer and shorter than 150 hours, this was evaluated as "Δ," and when the endurance time was shorter than 100 hours, this was evaluated as "x."

The results are shown in Table 1.

(Octacosane Adhesion Test)

In the same manner as in the evaluation of the silicone contamination resistance described above, a magnetic recording medium in which a lubricating layer including the compound 2a was formed was produced.

Separately, a jig in which a recess with a diameter of 4.5 mm and a height of 0.5 mm was formed was prepared, 10 μL of a 50 ppm octacosane ($C_{28}H_{58}$) solution (solvent hexane) was added dropwise into a hole thereof, and hexane was completely evaporated.

Next, on the jig containing octacosane, a magnetic recording medium in which a lubricating layer was formed was covered.

Next, the magnetic recording medium was put into a glass petri dish together with the jig, and additionally wrapped with aluminum foil and heated at 80° C. for 24 hours and then left at room temperature for 24 hours.

Then, the entire surface of the magnetic recording medium on the side facing the jig was observed by an optical surface analyzer (OSA: Candela 6300, commercially available from KLA Tencor).

In the observation by the OSA, when a scattered light intensity of a divided micro area exceeded a certain intensity, this was counted as one, and the number of scattered light beams was measured. When the lubricating layer including the compound 2a was uniform without gaps (a coating coverage was high), since adhesion of the vaporized octacosane to the magnetic recording medium was prevented, the number of counts was reduced. On the other hand, when there were gaps in the lubricating layer including the compound 2a, since the vaporized octacosane adhered to the surface of the magnetic recording medium to form a crystal, and light was strongly scattered, the number of counts of scattered light increased.

When the number of scattered light beams was less than 100, this was evaluated as "○," when the number of scattered light beams was 100 or more and less than 500, this was evaluated as "Δ," when the number of scattered light beams was 500 or more, this was evaluated as "x."

The results are shown in Table 1.

Example 2

Under a nitrogen atmosphere, the compound 2a (4 g) and 40 mL of t-butanol were put into a 20 mL eggplant flask and the mixture was stirred until it became uniform.

Next, 0.5 g of potassium tert-butoxide was added to the mixture, and 250 μL of glycidol was added thereto while heating at 70° C. and stirred for 8 hours.

Then, the mixture was cooled to 25° C. and neutralized with hydrochloric acid, and a fluorinated solvent (product name: Asahiklin AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator, a supercritical extraction was then performed under conditions of 60° C. and 18 MPa. and thereby a colorless and transparent liquid compound 3a (2 g) including a compound represented by the following Formula (10) was obtained. Here, $Rf^1$ in the following Formula (10) is represented by Formula (11).

$^1$H-NMR measurement and $^{19}$F-NMR measurement of the obtained compound 3a were performed, and the structure was identified based on the following results.

$^1$H-NMR (400 MHz, hexafluorobenzene/acetone-$D_6$=4/1 (v/v)): δ(ppm)=3.70 to 4.04 (20H), 4.05 to 4.22 (12H)

$^{19}$F-NMR (400 MHz, hexafluorobenzene/acetone-D6=4/1 (v/v)): δ(ppm)=−124.09 (4F), −120.70 (4F), −91.00 to −88.49 (27F), −80.61 (4F), −78.58 (4F), −55.65 to −51.37 (12F)

In addition, using the compound 3a, in the same manner as in Example 1, a lubricating layer including the compound 3a was formed on the magnetic recording medium, and in the same manner as in Example 1, the silicone contamination resistance of the compound 3a was evaluated, and an octacosane adhesion test was performed. The results are shown in Table 1.

[Chem. 34]

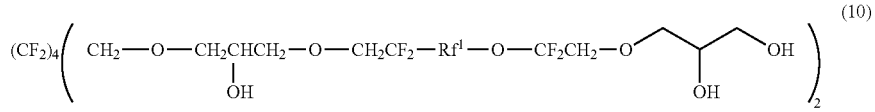

(10)

Example 3

Under a nitrogen atmosphere, the compound 2a (4.5 g) and 59 mL of t-butanol were put into a 300 mL eggplant flask, and the mixture was stirred until it became uniform.

Next, 4.3 g of epibromohydrin and 0.7 g of potassium tert-butoxide were sequentially added to the mixture, and stirred for 9 hours while heating at 70° C.

Then, the mixture was cooled to 25° C., a fluorinated solvent (product name: Asahiklin (registered trademark) AK-225, commercially available from AGC Inc.) was added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator, and column purification was additionally performed, and thereby a light yellow liquid compound 4a (4.5 g) including a compound represented by the following Formula (19) was obtained. Here. $Rf^1$ in the following Formula (19) is represented by Formula (11).

$^1$H-NMR measurement and $^{19}$F-NMR measurement of the obtained compound 4a were performed and the structure was identified based on the following results.

$^1$H-NMR (400 MHz, hexafluorobenzene/acetone-D$_6$=4/1 (v/v)): δ(ppm)=2.58 to 2.64 (2H), 2.75 to 2.81 (2H), 3.08 to 3.17 (2H), 3.58 (2H), 3.70 to 4.25 (24H)

$^{19}$F-NMR (400 MHz, hexafluorobenzene/acetone-D6=4/1 (v/v)): δ(ppm)=−124.10 (4F), −120.72 (4F), −91.00 to −88.49 (27F), −80.70 (2F), −80.58 (2F), −78.69 (2F), −78.58 (2F), −55.65 to −51.37 (12F)

[Chem. 35]

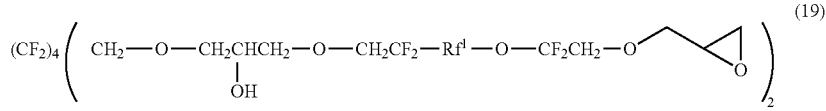

Under a nitrogen atmosphere, the compound 4a (4.3 g) and 74 mL of t-butanol were put into a 300 mL eggplant flask and the mixture was stirred until it became uniform.

Next, 4.4 g of 2,2,3,3-fluorobutane-1,4-diol and 0.8 g of potassium tert-butoxide were sequentially added to the mixture and stirred for 9 hours while heating at 70° C.

Then, the mixture was cooled to 25° C. and neutralized with hydrochloric acid, and a fluorinated solvent (product name: Asahiklin AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator, a supercritical extraction was then performed under conditions of 60° C. and 18 MPa, and thereby a colorless and transparent liquid compound 5a (3.5 g) including a compound represented by the following Formula (12) was obtained. Here, Rf$^1$ in the following Formula (12) is represented by Formula (11).

$^1$H-NMR and $^{19}$F-NMR measurements of the obtained compound 5a were performed and the structure was identified based on the following results.

$^1$H-NMR (400 MHz, hexafluorobenzene/acetone-D$_6$=4/1 (v/v)): δ(ppm)=3.67 to 4.05 (24H), 4.05 to 4.22 (16H)

$^{19}$F-NMR (400 MHz, hexafluorobenzene/acetone-D$_6$=4/1 (v/v)): δ(ppm)=−125.27 (4F), −124.09 (4F), −123.31 (4F), −120.70 (4F), −91.00 to −88.49 (27F), −80.55 (4F), −78.55 (4F), −55.65 to −51.37 (12F)

In addition, using the compound 5a, in the same manner as in Example 1, a lubricating layer including the compound 5a was formed on the magnetic recording medium, and in the same manner as in Example 1, the silicone contamination resistance of the compound 5a was evaluated, and an octacosane adhesion test was performed. The results are shown in Table 1.

Example 4

Under a nitrogen atmosphere, the compound 1 (1 g) and 22 g of a fluoropolyether represented by HO—CH$_2$CF$_2$(OCF$_2$CF$_2$)$_m$OCF$_2$CH$_2$OH (m=1 to 9, a number-average molecular weight of 800 and a molecular weight distribution of 1.02) were put into a 100 mL eggplant flask, and the mixture was stirred until it became uniform.

Next, 1.8 g of potassium tert-butoxide was added to the mixture and stirred for 8 hours while heating at 70° C.

Then, the mixture was cooled to 25° C. and neutralized with hydrochloric acid, and a fluorinated solvent (product name: Asahiklin (registered trademark) AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator and supercritical extraction was then performed under conditions of 60° C. and 18 MPa. and thereby a colorless and transparent liquid compound 2b (4.4 g) including a compound represented by the following Formula (13) was obtained. Here, Rf$^2$ in the following Formula (13) is represented by the following Formula (14).

$^1$H-NMR and $^{19}$F-NMR measurements of the obtained compound 2b were performed and the structure was identified based on the following results.

$^1$H-NMR (400 MHz, hexafluorobenzene/acetone-D6=4/1 (v/v)): δ(ppm)=3.71 to 3.89 (8H), 3.88 to 4.04 (6H), 4.05 to 4.22 (8H)

$^{19}$F-NMR (400 MHz, hexafluorobenzene/acetone-D6=4/1 (v/v)): δ(ppm)=−124.09 (4F), −120.70 (4F), −91.00 to −88.49 (40F), −81.13 (4F), −78.58 (4F)

In addition, using the compound 2b, in the same manner as in Example 1, a lubricating layer including the compound 2b was formed on the magnetic recording medium, and in the same manner as in Example 1, the silicone contamina-

[Chem. 36]

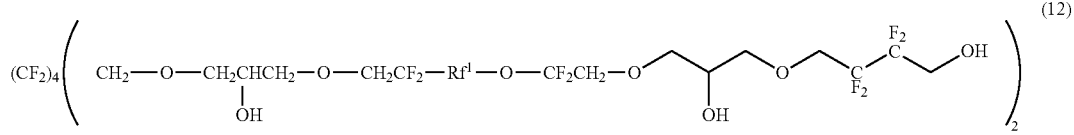

tion resistance of the compound 2b was evaluated, and an octacosane adhesion test was performed. The results are shown in Table 1.

[Chem. 37]

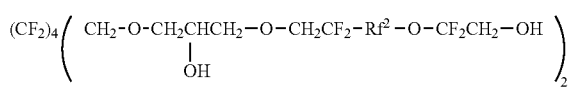
(13)

[Chem. 38]

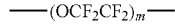
(14)

Example 5

Under a nitrogen atmosphere, the compound 2b (4 g) and 40 mL of t-butanol were put into a 20 mL eggplant flask, and the mixture was stirred until it became uniform.

Next, 0.5 g of potassium tert-butoxide was added to the mixture and 250 μL of glycidol was added thereto while heating at 70° C. and stirred for 8 hours.

Then, the mixture was cooled to 25° C. and neutralized with hydrochloric acid, and a fluorinated solvent (product name: Asahiklin (registered trademark) AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator, supercritical extraction was then performed under conditions of 60° C. and 18 MPa, and thereby a colorless and transparent liquid compound 3b (2.2 g) including a compound represented by the following Formula (15) was obtained. Here, Rf$^2$ in the following Formula (15) is represented by Formula (14).

$^1$H-NMR and $^{19}$F-NMR measurements of the obtained compound 3b were performed and the structure was identified based on the following results.

$^1$H-NMR (400 MHz, hexafluorobenzene/acetone-D6=4/1 (v/v)): δ(ppm)=3.71 to 3.89 (8H), 3.88 to 4.04 (6H), 4.04 to 4.24 (8H)

$^{19}$F-NMR (400 MHz, hexafluorobenzene/acetone-D$_6$=4/1 (v/v)): δ(ppm)=−124.09 (4F), −120.70 (4F), −91.00 to −88.49 (40F), −78.58 (8F)

In addition, using the compound 3b, in the same manner as in Example 1, a lubricating layer including the compound 3b was formed on the magnetic recording medium, and in the same manner as in Example 1, the silicone contamination resistance of the compound 3b was evaluated, and an octacosane adhesion test was performed. The results are shown in Table 1.

[Chem. 39]

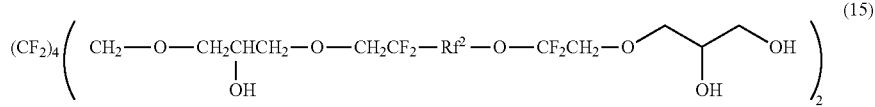
(15)

Example 6

Under a nitrogen atmosphere, the compound 2b (4.2 g) and 58 mL of t-butanol were put into a 300 mL eggplant flask, and the mixture was stirred until it became uniform.

Next, 4.1 g of epibromohydrin and 0.7 g of potassium tert-butoxide were sequentially added to the mixture, and the mixture was stirred for 9 hours while heating at 70° C.

Then, the mixture was cooled to 25° C., a fluorinated solvent (product name: Asahiklin (registered trademark) AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator and thereby a colorless and transparent liquid compound 4b (4.1 g) including a compound represented by the following Formula (20) was obtained. Here, Rf$^2$ in the following Formula (20) is represented by Formula (14).

$^1$H-NMR measurement and $^{19}$F-NMR measurement of the obtained compound 4b were performed, and the structure was identified based on the following results.

$^1$H-NMR (400 MHz, hexafluorobenzene/acetone-D$_6$=4/1 (v/v)): δ(ppm)=2.58 to 2.64 (2H), 2.75 to 2.81 (2H), 3.08 to 3.17 (2H), 3.58 (2H), 3.70 to 4.25 (24H)

$^{19}$F-NMR (400 MHz, hexafluorobenzene/acetone-D6=4/1 (v/v)): δ(ppm)=−124.09 (4F), −120.70 (4F), −91.00 to −88.49 (40F), −78.71 (4F), −78.58 (4F)

[Chem. 40]

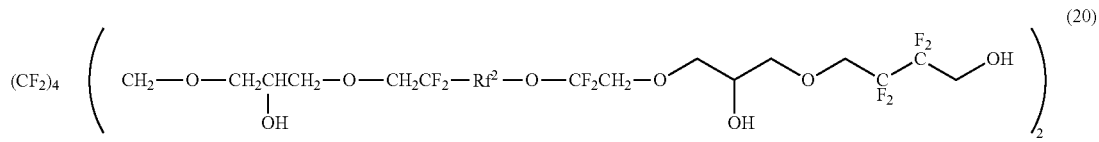
(20)

Under a nitrogen atmosphere, the compound 4b (4.0 g) and 70 mL of t-butanol were put into a 300 mL eggplant flask, and the mixture was stirred until it became uniform.

Next, 4.2 g of 2,2,3,3-fluorobutane-1,4-diol and 0.7 g of potassium tert-butoxide were sequentially added to the mixture and stirred for 9 hours while heating at 70° C.

Then, the mixture was cooled to 25° C. and neutralized with hydrochloric acid, and a fluorinated solvent (product name: Asahiklin (registered trademark) AK-225, commercially available from AGC Inc.) was then added thereto, and the mixture was washed with water.

Next, an organic phase in the eggplant flask was collected and sodium sulfate was added to the organic phase for dehydration and filtration was performed by a filter.

Next, the solvent was distilled off from the filtrate using an evaporator, supercritical extraction was then performed under conditions of 60° C. and 18 MPa, and thereby a colorless and transparent liquid compound 5b (3.4 g) including a compound represented by the following Formula (16) was obtained. Here, $Rf^2$ in the following Formula (16) is represented by Formula (14).

$^1$H-NMR measurement and $^{19}$F-NMR measurement of the obtained compound 5b were performed and the structure was identified based on the following results.

$^1$H-NMR (400 MHz, hexafluorobenzene/acetone-D6=4/1 (v/v)): δ(ppm)=3.67 to 4.05 (24H), 4.05 to 4.22 (16H)

$^{19}$F-NMR (400 MHz, hexafluorobenzene/acetone-D6=4/1 (v/v)): δ(ppm)=−125.27 (4F), −124.09 (4F), −123.31 (4F), −120.70 (4F), −91.00 to −88.49 (40F), −78.68 (4F), −78.55 (4F)

In addition, using the compound 5b, in the same manner as in Example 1, a lubricating layer including the compound 5b was formed on the magnetic recording medium, and in the same manner as in Example 1, the silicone contamination resistance of the compound 5b was evaluated, and an octacosane adhesion test was performed. The results are shown in Table 1.

[Chem. 41]

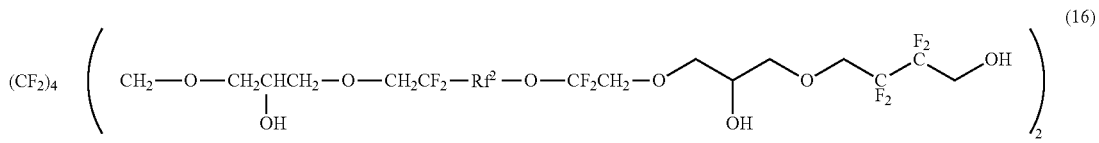
(16)

COMPARATIVE EXAMPLE

Using Fomblin Z-tetraol commercially available from Solvey Solexis (with a molecular weight of about 2,000, shown in the following Formula (21)), in the same manner as in Example 1, a lubricating layer including the compound was formed on the magnetic recording medium, and in the same manner as in Example 1, the silicone contamination resistance of the compound was evaluated and an octacosane adhesion test was performed. The results are shown in Table 1.

[Chem. 42]

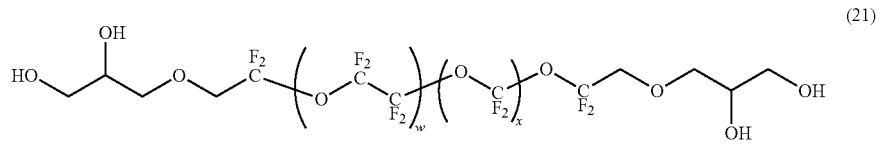
(21)

TABLE 1

| | Film thickness of lubricating layer (Å) | Silicone contamination resistance | | Octacosane adhesion test | |
|---|---|---|---|---|---|
| | | Endurance time (hr) | Evaluation | Number of scattered light beams (number) | Evaluation |
| Example 1 | 10 | 276 | ○ | 88 | ○ |
| Example 2 | 11 | 591 | ○ | 23 | ○ |
| Example 3 | 10 | 647 | ○ | 11 | ○ |
| Example 4 | 11 | 263 | ○ | 105 | Δ |
| Example 5 | 10 | 455 | ○ | 44 | ○ |
| Example 6 | 11 | 513 | ○ | 27 | ○ |
| Comparative Example | 12 | 48 | x | 1,890 | x |

Based on the results in Table 1, it was found that, when the lubricating layer was formed on the magnetic medium using the compounds of Examples 1 to 6, the surface of the magnetic recording medium was covered with a higher coverage and the silicone contamination resistance was considerably better than when the lubricating layer was formed on the magnetic medium using the compound of the comparative example.

INDUSTRIAL APPLICABILITY

When the lubricant for a magnetic recording medium of the present invention is used, even if the thickness is thin, it is possible to form a lubricating layer that can cover the surface of the protective layer of the magnetic recording medium with high coverage.

REFERENCE SIGNS LIST

10 Magnetic recording medium
11 Substrate
12 Adhesion layer
13 Soft magnetic layer
14 First underlayer
15 Second underlayer
16 Magnetic layer
17 Protective layer
18 Lubricating layer

The invention claimed is:
1. A fluorine-containing ether compound represented by the following General Formula (1):

[Chem. 1]

$$(F_2C\!\!-\!\!)_l\!\!-\!\!A\!\!-\!\!B\!\!-\!\!D)_2 \quad (1)$$

(in the formula, A is a linking group represented by the following Formula (9), B is any of the following Formula (2), the following Formula (3), the following Formula (4) and the following Formula (5), D is any of a hydroxyl group, the following Formula (6), the following Formula (7) and the following Formula (8), and l is an integer of 1 to 10),

[Chem. 2]

$$-\!\!O\!\!-\!\!\underset{H_2}{C}\!\!-\!\!\underset{F_2}{C}\!\!-\!\!\left(\!\!O\!\!-\!\!\underset{F_2}{C}\!\!-\!\!\underset{F_2}{C}\!\!\right)_{\!\!m}\!\!\left(\!\!O\!\!-\!\!\underset{F_2}{C}\!\right)_{\!\!n}\!\!-\!\!O\!\!-\!\!\underset{F_2}{C}\!\!-\!\!\underset{H_2}{C}\!\!-\quad (2)$$

(in the formula, m is an integer of 1 to 30, and n is an integer of 1 to 30),

[Chem. 3]

$$-\!\!O\!\!-\!\!\underset{H_2}{C}\!\!-\!\!\underset{F_2}{C}\!\!-\!\!\left(\!\!O\!\!-\!\!\underset{F_2}{C}\!\!-\!\!\underset{F_2}{C}\!\!\right)_{\!\!m}\!\!-\!\!O\!\!-\!\!\underset{F_2}{C}\!\!-\!\!\underset{H_2}{C}\!\!-\quad (3)$$

(in the formula, m is an integer of 1 to 30),

[Chem. 4]

$$-\!\!O\!\!-\!\!\underset{H_2}{C}\!\!-\!\!\underset{F_2}{C}\!\!-\!\!\underset{F_2}{C}\!\!-\!\!\left(\!\!O\!\!-\!\!\underset{F_2}{C}\!\!-\!\!\underset{F_2}{C}\!\!-\!\!\underset{F_2}{C}\!\!\right)_{\!\!p}\!\!-\!\!O\!\!-\!\!\underset{F_2}{C}\!\!-\!\!\underset{F_2}{C}\!\!-\!\!\underset{H_2}{C}\!\!-\quad (4)$$

(in the formula, p is an integer of 1 to 30),

[Chem. 5]

$$-\!\!O\!\!-\!\!\underset{F}{\overset{CF_3}{\underset{|}{C}}}\!\!H_2\!\!-\!\!\left(\!\!O\!\!-\!\!\underset{F}{\overset{CF_3}{\underset{|}{C}}}\!\!-\!\!\underset{F_2}{C}\!\!\right)_{\!\!q}\!\!-\!\!O\!\!-\!\!\underset{F}{\overset{CF_3}{\underset{|}{C}}}\!\!-\!\!\underset{H_2}{C}\!\!-\quad (5)$$

(in the formula, q is an integer of 1 to 30),

[Chem. 6]

$$\diagdown\!\!O\!\!-\!\!CH_2\!\!-\!\!\underset{OH}{CH}\!\!-\!\!CH_2\!\!-\!\!\left(\!\!O\!\!-\!\!CH_2\!\!-\!\!\underset{OH}{CH}\!\!-\!\!CH_2\!\!\right)_{\!\!r}\!\!-\!\!OH \quad (6)$$

(in the formula, r is an integer of 0 to 5),

[Chem. 7]

$$\diagdown\!\!O\!\!-\!\!CH_2\!\!-\!\!\underset{OH}{CH}\!\!-\!\!CH_2\!\!-\!\!O\!\!-\!\!(CH_2)_s CH_2OH \quad (7)$$

(in the formula, s is an integer of 0 to 5),

[Chem. 8]

$$\diagdown\!\!O\!\!-\!\!CH_2\!\!-\!\!\underset{OH}{CH}\!\!-\!\!CH_2\!\!-\!\!O\!\!-\!\!(CF_2)_t CH_2OH \quad (8)$$

(in the formula, t is an integer of 1 to 5),

[Chem. 9]

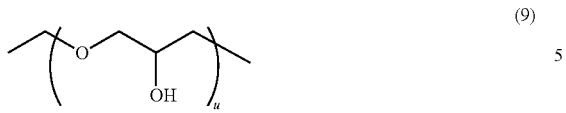
(9)

(in the formula, u is an integer of 1).

2. The fluorine-containing ether compound according to claim 1,
wherein the number-average molecular weight is in a range of 1,000 to 10,000.

3. The fluorine-containing ether compound according to claim 1,
wherein the compound represented by General Formula (1) is represented by the following Formula (10):

[Chem. 10]

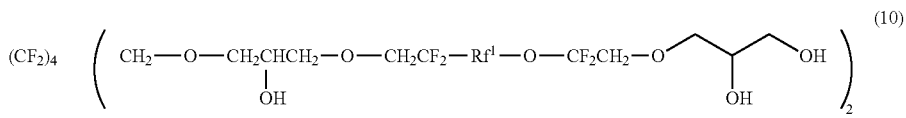
(10)

(in the formula, $Rf^1$ is represented by the following Formula (11), and each of m and n is an integer of 1 to 30),

[Chem. 11]

(11)

4. The fluorine-containing ether compound according to claim 1,
wherein the compound represented by General Formula (1) is represented by the following Formula (12):

[Chem. 12]

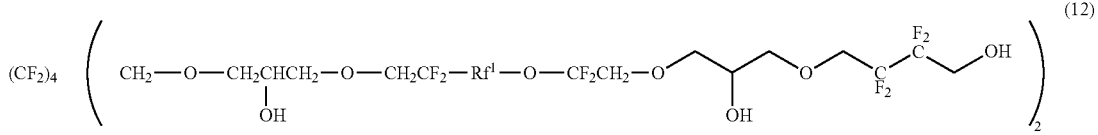
(12)

(in the formula, $Rf^1$ is represented by the following Formula (11), and each of m and n is an integer of 1 to 30),

[Chem. 13]

(11)

5. The fluorine-containing ether compound according to claim 1,
wherein the compound represented by General Formula (1) is represented by the following Formula (13):

[Chem. 14]

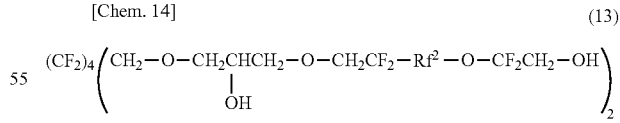
(13)

(in the formula, $Rf^2$ is represented by the following Formula (14), and m is an integer of 1 to 30),

[Chem. 15]

(14)

6. The fluorine-containing ether compound according to claim 1,
wherein the compound represented by General Formula (1) is represented by the following Formula (15):

[Chem. 16]

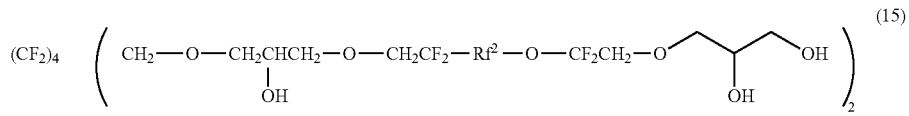
(15)

(in the formula, Rf² is represented by the following Formula (14), and m is an integer of 1 to 30)

[Chem. 17]

—(OCF$_2$CF$_2$)$_m$— (14)

7. The fluorine-containing ether compound according to claim 1,
wherein the compound represented by General Formula (1) is represented by the following Formula (16):

[Chem. 18]

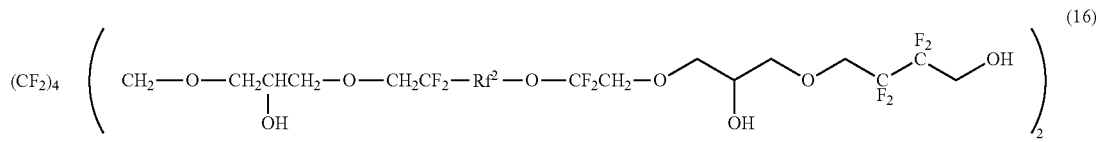
(16)

(in the formula, Rf² is represented by the following Formula (14), and m is an integer of 1 to 30),

[Chem. 19]

—(OCF$_2$CF$_2$)$_m$— (14)

8. The fluorine-containing ether compound according to claim 1,
wherein the compound represented by General Formula (1) is represented by the following Formula (17):

[Chem. 20]

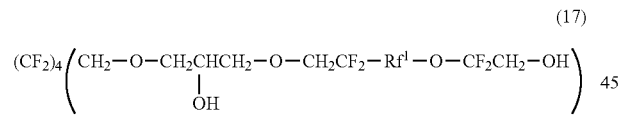
(17)

(in the formula, Rf¹ is represented by the following Formula (11), and m and n are integers of 1 to 30),

[Chem. 21]

—(OCF$_2$CF$_2$)$_m$(OCF$_2$)$_n$— (11)

9. A lubricant for a magnetic recording medium comprising the fluorine-containing ether compound according to claim 1.

10. A magnetic recording medium in which at least a magnetic layer, a protective layer, and a lubricating layer are sequentially provided on a substrate,
wherein the lubricating layer consists of the lubricant for a magnetic recording medium according to claim 9.

11. The magnetic recording medium according to claim 10,
wherein the average film thickness of the lubricating layer is 0.5 nm to 3 nm.

* * * * *